(12) United States Patent
Osborne

(10) Patent No.: US 7,311,697 B2
(45) Date of Patent: Dec. 25, 2007

(54) CENTRAL VENOUS CATHETER

(75) Inventor: Thomas A. Osborne, Bloomington, IN (US)

(73) Assignee: Cook Critical Care Incorporated, Bloomington, IN (US)

( * ) Notice: Subject to any disclaimer, the term of this patent is extended or adjusted under 35 U.S.C. 154(b) by 331 days.

(21) Appl. No.: 10/878,752

(22) Filed: Jun. 28, 2004

(65) Prior Publication Data

US 2005/0004554 A1   Jan. 6, 2005

Related U.S. Application Data

(60) Provisional application No. 60/484,427, filed on Jul. 2, 2003.

(51) Int. Cl.
*A61M 25/00* (2006.01)

(52) U.S. Cl. .................................... 604/524

(58) Field of Classification Search ............... 604/524, 604/523, 525, 526, 43, 528, 95.04, 95.05, 604/530, 531, 536

See application file for complete search history.

(56) References Cited

U.S. PATENT DOCUMENTS

| | | | |
|---|---|---|---|
| 4,543,087 A | 9/1985 | Sommercorn et al. | |
| 4,682,978 A | 7/1987 | Martin | |
| 4,755,176 A | 7/1988 | Patel | |
| 4,968,307 A * | 11/1990 | Dake et al. ............... | 604/264 |
| 4,995,865 A | 2/1991 | Gahara et al. | |
| 4,998,923 A | 3/1991 | Samson et al. | |
| 5,205,830 A | 4/1993 | Dassa et al. | |
| 5,250,038 A | 10/1993 | Melker et al. | |
| 5,318,032 A | 6/1994 | Lonsbury et al. | |
| 5,329,923 A | 7/1994 | Lundquist | |
| 5,378,230 A | 1/1995 | Mahurkar | |
| 5,454,795 A | 10/1995 | Samson | |
| 5,477,856 A | 12/1995 | Lundquist | |
| 5,573,520 A | 11/1996 | Schwartz et al. | |
| 5,833,645 A * | 11/1998 | Lieber et al. ............... | 604/509 |
| 5,851,203 A | 12/1998 | van Muiden | |
| 5,947,940 A * | 9/1999 | Beisel ......................... | 604/526 |

(Continued)

FOREIGN PATENT DOCUMENTS

EP   0 993 837 A1   4/2000

(Continued)

OTHER PUBLICATIONS

Cook Spectrum Catalog, www.cookgroup.com, Bloomington, Indiana, 1999.

*Primary Examiner*—Nicholas D. Lucchesi
*Assistant Examiner*—Christopher D. Koharski
(74) *Attorney, Agent, or Firm*—Brinks Hofer Gilson Lione

(57) ABSTRACT

A central venous catheter comprises a catheter body having a plurality of lumens extending longitudinally therein. At least one of the lumens extends longitudinally through the catheter body from its proximal end to an exit port at its distal end, and at least one other lumen extends longitudinally through the catheter body to a closed distal portion of the catheter body. The catheter body further includes a sideport positioned to establish communication between the closed-end lumen and an area exterior to the catheter body. The catheter body further includes a flexible member, such as a coiled spring, in the closed-end lumen in a space between the sideport and the closed end.

23 Claims, 2 Drawing Sheets

U.S. PATENT DOCUMENTS

| | | |
|---|---|---|
| 6,206,849 B1 * | 3/2001 | Martin et al. .................. 604/43 |
| 6,217,565 B1 | 4/2001 | Cohen |
| 6,299,598 B1 * | 10/2001 | Bander .................. 604/101.03 |
| 6,319,244 B2 | 11/2001 | Suresh et al. |
| 6,569,150 B2 | 5/2003 | Teague et al. |
| 6,676,643 B2 * | 1/2004 | Brushey ..................... 604/264 |
| 2001/0034514 A1 | 10/2001 | Parker |
| 2002/0032408 A1 | 3/2002 | Parker et al. |
| 2002/0042593 A1 | 4/2002 | Mickley et al. |
| 2002/0161353 A1 | 10/2002 | Kortelling |
| 2003/0073976 A1 | 4/2003 | Brushey |
| 2003/0191450 A1 | 10/2003 | Teague et al. |

FOREIGN PATENT DOCUMENTS

| | | |
|---|---|---|
| FR | 2 512 665 | 8/1982 |

* cited by examiner

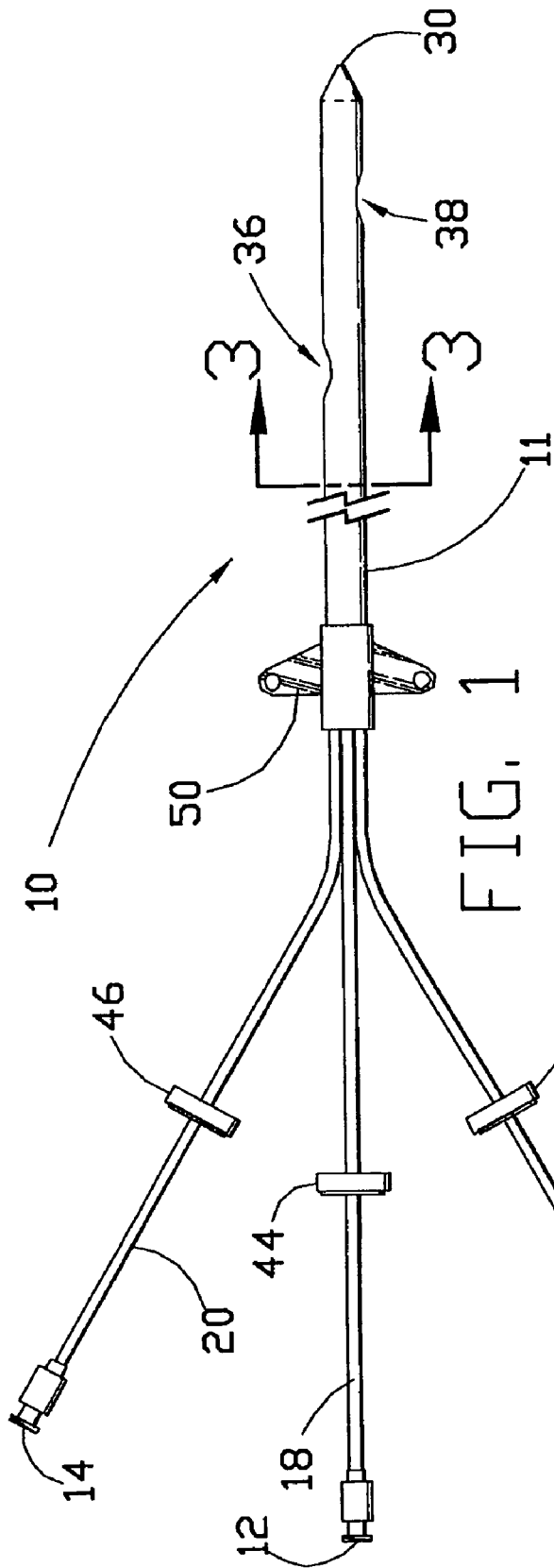
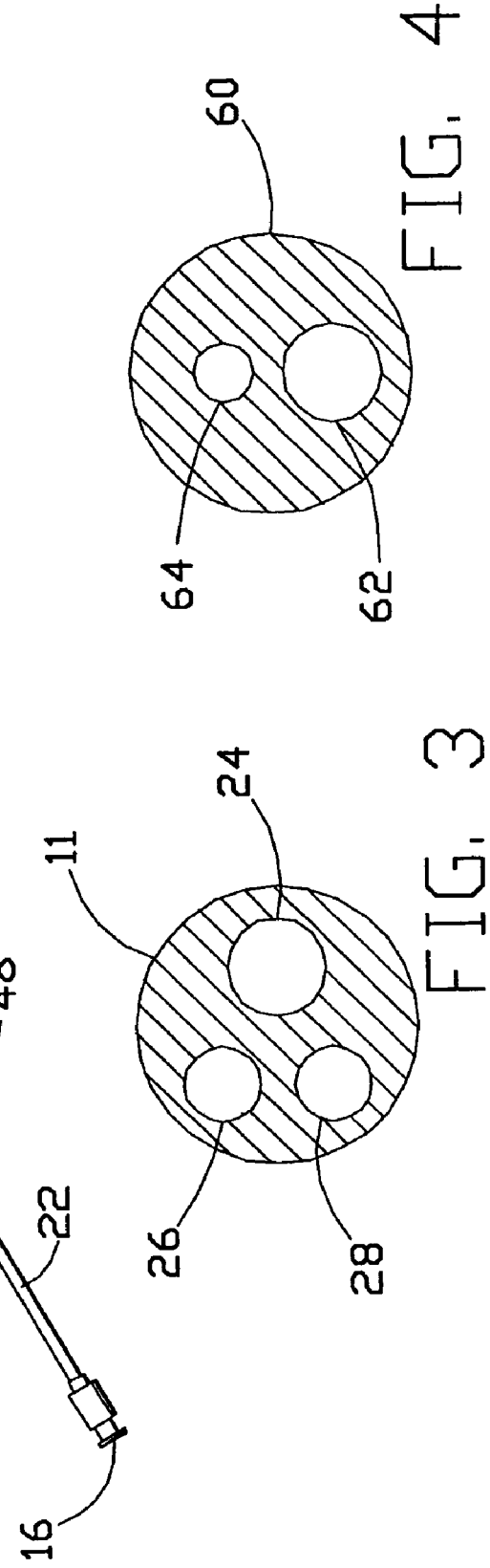

CENTRAL VENOUS CATHETER

RELATED APPLICATION

The present patent document claims the benefit of the filing date under 35 U.S.C. §119(e) of Provisional U.S. Patent Application Ser. No. 60/484,427, filed Jul. 2, 2003, which is hereby incorporated by reference.

BACKGROUND

1. Technical Field

The present invention relates generally to central venous catheters, and more particularly, to a central venous catheter having enhanced pushability.

2. Background Information

Central venous catheters are typically used for medical procedures such as blood pressure monitoring, blood sampling and the administration of drugs and fluids to a patient. Such procedures often require that the catheter be left indwelling in the patient for an extended period of time.

Generally, a central venous catheter is surgically inserted into a major vein, such as the superior vena cava. Such catheters are typically introduced using percutaneous entry techniques, such as the well-known Seldinger technique. In the Seldinger technique, the physician makes an oblique entry into the vein with a beveled needle. A wire guide is then inserted through the bore of the needle about 5 to 10 cm into the vein. The needle is thereafter withdrawn, leaving the wire guide in place. The catheter is then inserted over the wire guide, and advanced through the skin at the needle puncture site and into the vein. Once the catheter is in place within the vein, the wire guide is withdrawn. The Seldinger technique is a widely used procedure for introducing catheters and other interventional devices into the vasculature, and is normally carried out by the physician without complication.

Since the central venous catheter is left indwelling in the vein, it should be soft and flexible in order to prevent erosion of the vein wall at the tip of the catheter. However, since the catheter is soft and flexible, it does not have a great deal of column strength. When a central venous catheter is pushed into a puncture site, it is not uncommon for the catheter to encounter some resistance. If the pushability of the catheter isn't sufficient to overcome this resistance, the catheter may "bunch up" or "accordion" at the site of the resistance. Certain portions of the catheter are particularly prone to bunching up. One such area is in the vicinity of the catheter sideports. When sideports are present in a catheter, the cross-sectional area and strength of the catheter at these sites is reduced, due in part to the lack of catheter material at the sideport. As a result, even more resistance to insertion is incurred at such sites, and the catheter may eventually become lodged such that it cannot be advanced further into the vein.

In the past, the problem of lack of pushability of such catheters has generally been addressed in two ways. The first way has been to form the catheter from a material that has a high enough stiffness or durometer to allow for good pushability in the vein, thereby enabling it to overcome the resistance encountered in the vein. However, increasing the stiffness of a catheter is generally undesirable and can compromise the safety of the patient by increasing the likelihood that the stiff catheter will eventually erode through the wall of the vein.

The second way to address the pushability problem has been to fill in the "dead space" in the lumens in the catheter, thereby imparting extra strength and pushability to the distal end of the catheter. The term "dead space" is used in the catheter art to refer to the portion of a lumen in a multi-lumen catheter, other than the central lumen, that extends distally from a sideport and terminates at a closed end near the distal tip. The dead space in a lumen can be filled with additional material that has a stiffness substantially the same as the stiffness of the catheter material itself. The additional material can be the same material as the catheter, or another compatible material having comparable stiffness. In one known process, generally referred to as "beading", the additional material comprises beads that are inserted into the dead space at the sideport. Beading and similar approaches greatly increase the amount of material in the cross section at the tip area, and thereby make the catheter more pushable. However, the addition of beading to the dead space increases the stiffness of the tip area, even when the additional material is as soft as the catheter material itself. This increased stiffness increases the chance that the catheter tip will eventually erode the vein wall. In addition, the use of beading or extra plastic material to fill the space at the tip of the catheter is not an ideal solution because the addition of such material does not impart a great deal of extra column strength, and increases the stiffness of the catheter at the very portion that needs most to be flexible.

Central venous catheters generally have more than one lumen. Typically, such catheters have either two or three lumens. With multi-lumen catheters, one lumen may be used for pressure monitoring, another lumen may be used for drug or fluid infusion, and still another lumen may be used for blood sampling. The central lumen can additionally serve as the wire guide lumen during placement. As with other interventional devices, it is desirable that the lumens have the maximum cross-sectional diameter possible for a given catheter size so that optimal use can be made of available space. Thus, the amount of material utilized for the outer tube wall and the webbing between the lumens is preferably minimized to the greatest extent possible. However, minimizing the amount of material in the tubing wall and the webbing between the lumens also reduces the column strength, or pushability, of the catheter.

Accordingly, it is desired to provide a central venous catheter that has a high enough stiffness to allow for good pushability in the vein, and that does not involve the addition of a stiff catheter material or an appreciable amount of other material to the distal tip area of the catheter. It is further desired to provide a central venous catheter that has sufficient softness to minimize the possibility that the catheter will erode the wall of a vein.

BRIEF SUMMARY

The central venous catheter of the present invention addresses the problems of the prior art. The inventive catheter has sufficient stiffness to allow good pushability of the catheter into the vein, and yet retains sufficient softness to minimize the possibility that the catheter will erode through the wall of the vein.

In one form, the invention comprises a central venous catheter comprising a catheter body having a proximal end and a distal end, and having a plurality of lumens extending longitudinally therein. One of the lumens extends longitudinally through the catheter body from its proximal end to an exit port at its distal end. At least one other lumen extends longitudinally through the catheter body to a closed distal portion of the catheter body. The catheter body further includes a sideport positioned to establish communication between the other lumen and an area exterior to the catheter body. A segment of the other lumen disposed between the sideport and the closed end comprises a dead space, and the catheter body includes a flexible member, such as a coiled spring, in the dead space.

In another form thereof, the invention comprises a method for performing a medical interventional procedure. A catheter assembly is provided for use in the procedure. The catheter assembly comprises a catheter body having a proximal end and a distal end, and having a plurality of lumens extending longitudinally therein. A first lumen extends longitudinally through the catheter body from the proximal end to an exit port at the distal end, and a second lumen extends longitudinally through the catheter body to a closed distal portion of the catheter body. The catheter body further includes a sideport positioned along a length of the catheter body to establish communication between the second lumen and an area exterior to the catheter body. The second lumen includes a dead space disposed between the sideport and the closed distal portion, and further includes a flexible member disposed in the dead space. This catheter assembly is inserted into a body vessel, and is utilized therein for performing an interventional procedure.

BRIEF DESCRIPTION OF THE DRAWINGS

FIG. 1 is an elevational view of a triple lumen central venous catheter according to an embodiment of the present invention;

FIG. 3 is a sectional view along line 3-3 of FIG. 1.

FIG. 4 is a sectional view of a dual lumen catheter.

DETAILED DESCRIPTION OF THE DRAWINGS AND THE PRESENTLY PREFERRED EMBODIMENTS

Figure 2:
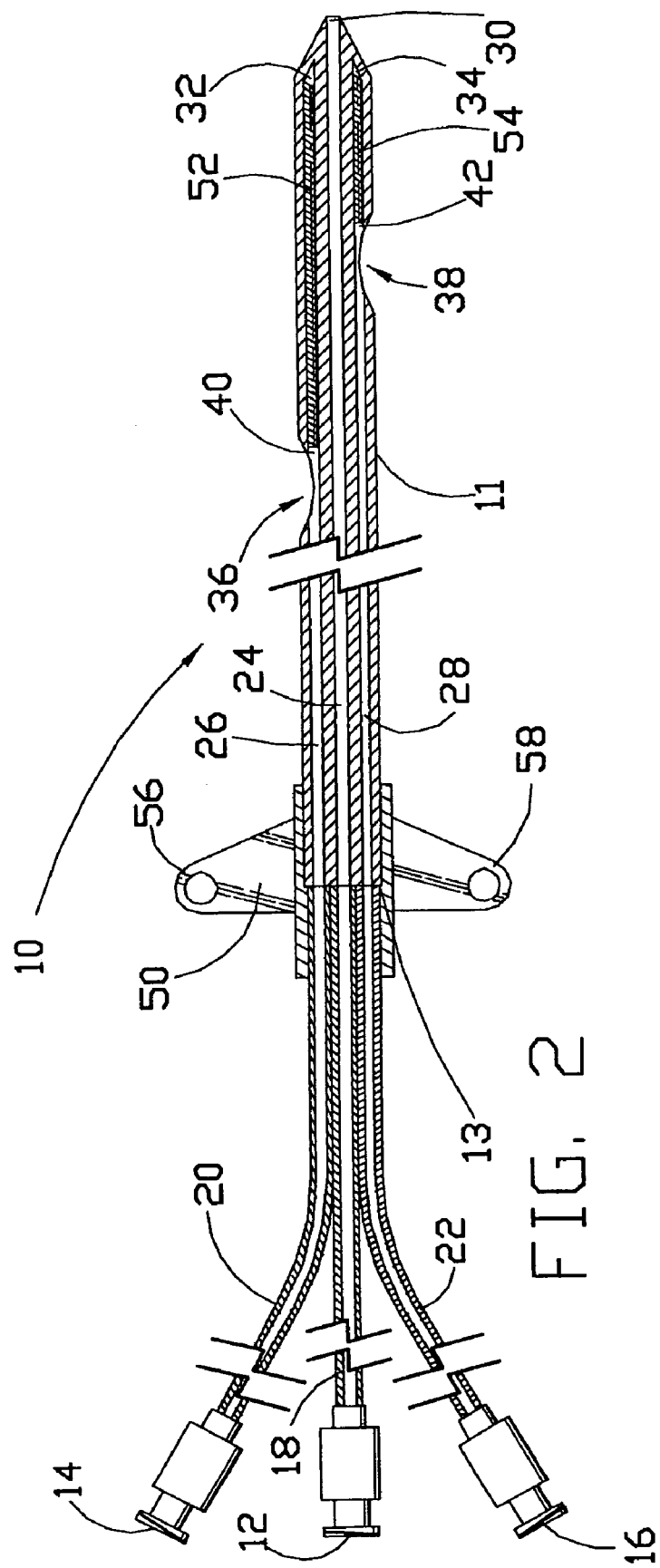
FIG. 2 is a longitudinal view, partially in section, of the triple lumen central venous catheter of FIG. 1.

FIG. 1 is an elevational view of one embodiment of a central venous catheter 10 for use in a medical interventional procedure according to the present invention. As used herein, the term "medical interventional procedure" refers to a procedure of the type in which central venous catheters are commonly used. Non-limiting examples of such procedures include blood pressure monitoring, blood sampling, and the administration of drugs and/or fluids to a patient. Typically, such procedures necessitate that the catheter be left indwelling in the body vessel for an extended period of time.

FIG. 2 is a schematic longitudinal sectional view of the catheter of FIG. 1, and FIG. 3 is a sectional view along lines 3-3 of FIG. 1. FIG. 4 is a sectional view of a central venous catheter 60 similar to the catheter of FIG. 1, but having two lumens. Central venous catheters 10, 60 may be used, for example, for blood pressure monitoring, blood sampling, or the administration of drugs and/or fluids to a patient.

Although central venous catheters may have only a single lumen that extends longitudinally all of the way through the catheter body, it is more common that such catheters have multiple lumens, and it is most common that the catheters have either two or three lumens. The present invention relates to such multi-lumen catheters. With multi-lumen catheters, it is common that the outer wall of the catheter includes at least one sideport. The sideport establishes communication between a lumen and the environment exterior to the catheter. In this manner, drugs and/or fluids can be introduced into the catheter through entry ports proximal to the catheter, and pass from the catheter lumen through the sideports to the vessel in which the catheter has been placed. In order to space the portions of the vessel that receive the drugs and/or fluids, the sideports of respective lumens are normally provided at different axial locations along the length of the catheter. A particular lumen can be provided with more than one sideport, however it is more common that a lumen have only a single sideport.

The central venous catheter 10 shown in the embodiment of FIGS. 1-3 is a triple lumen catheter. In the embodiment shown, triple lumen catheter 10 comprises three separate noncommunicating lumens 24, 26, 28 that extend longitudinally through body 11 of catheter 10. Catheter 10 further includes entry ports 12, 14, 16. In the embodiment shown, entry ports 12, 14, 16 communicate with respective lumens 24, 26, 28 in catheter body 11 via respective extension tubes 18, 20, 22.

In the triple lumen catheter depicted in FIG. 1, central lumen 24 extends longitudinally from the proximal end 13 of catheter body 11 to exit opening 30 disposed at the distal end of body 11. In the following discussion, the terms "proximal" and "distal" will be used to describe the axial ends of the apparatus, as well as the axial ends of various component features. The term "proximal end" refers to the end of the central venous catheter (or component) that is closest to the operator during use of the assembly. The term "distal end" refers to the end of the central venous catheter (or component) that is inserted into the patient, or that is closest to the patient. In the orientation of central venous catheter 10 and each of its component features shown in FIGS. 1 and 2, the proximal end is to the left, while the distal end is to the right.

Unlike lumen 24, lumens 26, 28 do not terminate at exit openings. Rather, lumen 26 extends longitudinally from catheter body proximal end 13 and terminates at closed distal end 32. Lumen 28 extends longitudinally from proximal end 13 and terminates at closed distal end 34.

Catheter body 11 is provided with respective side openings, or "sideports", 36, 38. As best shown in FIG. 2, sideports 36, 38 are openings that are cut or otherwise formed in catheter body 11 in known manner. Sideport 36 establishes communication between lumen 26 and the environment external to catheter 10. Sideport 38 establishes communication between lumen 28 and the environment external to catheter 10. Generally, this external environment comprises the internal passageway of a vessel into which the catheter has been inserted. In the embodiment shown, sideport 36 is referred to as the proximal sideport, while sideport 38 is referred to as the "mid" sideport. Drugs and/or fluids that are administered through entry ports 14, 16 pass through respective extension tubes 20, 22 and achieve vascular access through respective sideports 36, 38. Preferably, sideports 36, 38 are longitudinally separated, or spaced, an appropriate distance along the length of the catheter in proportion to the catheter's French size, in order to axially separate the distribution point of drugs and/or fluids that may be administered simultaneously, or substantially simultaneously, through the lumens. Multiple sideports may be provided, in which event the sideports may be oriented in a spiral or helical configuration along the catheter body, in order to further separate the distribution points of such drugs and/or fluids.

The area 40 of lumen 26 distal to the sideport 36, or in other words, between the sideport and closed end 32, comprises the "dead space" of lumen 26. The dead space is shown in FIG. 2. The area 42 of lumen 28 between sideport 38 and closed end 34 comprises the dead space of lumen 28. Since lumen 24 extends fully through catheter body 11 to exit opening 30, lumen 24 does not have a dead space. Exit opening 30 represents the most distal portion of catheter 10.

As shown in the embodiment of FIG. 1, slide clamps 44, 46, 48 or other known clamping or locking mechanisms may be provided on extension tubes 18, 20, 22, respectively. Slide clamps 44, 46, 48 are utilized to selectively clamp or unclamp the extension tubes between an "open" position and a "closed" position, to thereby control fluid flow through the lumen. In a preferred embodiment, catheter 10 further includes a hub 50. Hub 50 joins the respective distal ends of extension tubes 18, 20, 22 to the proximal end 13 of catheter body 11, to establish communication between the extension tubes and the appropriate lumen. Hub 50 preferably is provided with a pair of radially protruding wings 56, 58. Wings 56, 58 can be used as anchor points for securing the catheter in place after it has been inserted, such as by taping them to the patient's skin.

According to the present invention, a flexible wire or wire-like member is provided to fill a portion of the dead space 40, 42 in lumens 26, 28, respectively. In the embodiment shown, the flexible member comprises helical coils 52, 54. Helical coil 52 is provided in dead space area 40, and coil 54 is provided in dead space area 42. The use of this material to fill the dead space distal to the sideports provides enhanced pushability to the catheter without adding significant stiffness or bulk to the tip. When the flexible member comprises a helical coil, the coils may be simply inserted by any convenient means into the dead space through the sideports. In many cases, the shorter coil 54 will be between about 1 and 2 cm long, whereas the longer coil 52 will be between about 4 and 6 cm long, although longer, or shorter, coils may be provided in a particular case. Preferably, the coil will have a diameter selected such that the coil fits snugly in the lumen. Depending on catheter French size and lumen size, the coils could range, e.g., from about 0.018 inch (0.46 mm) to about 0.045 inch (1.14 mm) diameter. All dimensions provided herein are representative only, and in practice, actual dimensions can be longer, or shorter, than the specific dimensions listed herein.

It is well known that when the ends of a spring are pushed, the coils of the spring tend to stack and form a fairly rigid column. At the same time, springs can be easily bended without permanent deformation. These same properties have been recognized in the past in wire guide construction by making wire guides out of long thin tightly-wound coil springs. The presence of the springs thus imparts pushability to the catheter, and yet does not appreciably affect the hardness of the outer catheter body. In addition, the use of a spring enhances the kink resistance of the catheter.

Coils 52, 54 are preferably formed from stainless steel rectangular wire. Rectangular wire is known to provide favorable column strength. Alternatively, round wire may be favorably utilized in place of rectangular wire. Other types of wire commonly used in medical procedures may also be substituted. For example, metallic alloys, such as nitinol, may be used in place of stainless steel. Nitinol has good column strength and can be easily bent through the stress induced martensite state without permanent deformation. Alternatively, instead of using a coil spring, a cannula can be formed from a tubular material that has a helical shape cut into the distal portion of the cannula. Such shape may be cut by means well known in the art, such as by laser cutting. A cut cannula has properties similar to those of a spring. Those skilled in the art can readily envision other compositions that can be substituted for the compositions disclosed, all of which are considered within the scope of the invention. As a further variation of the invention, the coil can be bonded to the wall of the lumen along a part of the length of the coil, or along its entire length. Bonding the coil to the catheter wall would prevent the catheter material from sliding along the coil and "bunching up" when it meets resistance as it is pushed into the entry site.

FIG. 4 is a cross-sectional view of a dual lumen catheter 60. Dual lumen catheter 60 is generally similar to the triple lumen catheter of FIGS. 1-3, except that it is only provided with two lumens, identified in FIG. 4 as lumens 62, 64. Central lumen 62 extends longitudinally from the proximal end of the catheter body to an exit opening disposed at the distal end of the catheter body in the same manner as the catheter of FIGS. 1-3. Similarly, lumen 64 extends longitudinally from the catheter body proximal end and terminates at a closed distal end. In this embodiment, the flexible material is inserted into the dead space between the sideport of this lumen and the closed distal end of the catheter body.

Polymeric material used to form central venous catheter bodies often has a durometer of about 49 on the Shore D scale. This material is somewhat softer than might optimally be desired, which softness can make it difficult to insert in some circumstances. However, even though the material is softer than might optimally be desired, the soft durometer generally represents a favorable compromise, since it minimizes the possibility of vein perforation that may be present with higher durometer materials.

It would be preferred to use a material having an even lower durometer, such as about 25 to 30 on the Shore D scale. However, a soft material of this durometer would be difficult, if not impossible, to insert percutaneously. Similarly, materials in the 80 durometer range would be much easier to insert percutaneously, however these hard materials would carry a high risk of eroding through the vein wall after only a few days of indwelling in the patient. With the present invention, catheter materials having a variety of durometers can be used, including conventional 49 durometer material. Those skilled in the art can readily determine a favorable durometer for any particular catheter material without undue experimentation based upon the teachings of this invention.

If desired, central venous catheter 10 can be impregnated or coated with antimicrobials to minimize the risk of bacterial colonization of the catheter, and catheter-related bacteremia during use. An example of an antimicrobial impregnated catheter is the COOK SPECTRUM® central venous catheter, available from Cook Incorporated, of Bloomington, Ind. The SPECTRUM® catheter is impregnated with the antimicrobials minocycline and rifampin. Alternatively, other well-known antimicrobials may be substituted for minocycline and rifampin.

As stated previously, most central venous catheters in general medical usage have either two or three lumens. Multi-lumen catheters reduce the necessity of multiple venipunctures or multiple stopcock configurations that are generally required when a single lumen catheter is used. However, the teachings of the present invention are applicable to catheters having any number of lumens. For multi-lumen catheters, it is preferred to include a helical coil in the dead space area of each lumen having a dead space. However, this is not required. For example, if desired, a coil may be placed in a single dead space area, while the other dead space area(s) may be left empty, or may be beaded or otherwise loaded in a manner described previously.

Similarly, it is preferred that the coil occupy all, or substantially all, of the dead space area into which it is inserted. However, this is also not required. Rather, the coil or other filler material need only occupy a portion of the dead space area. However, for best results, it is believed that the coil should occupy all, or substantially all, of the dead space area.

Central venous catheters according to the present invention may be provided in a variety of sizes as are presently used for such catheters. The central venous catheter may be made of any conventional material commonly used in the catheter art. A preferred catheter composition is polyurethane. Other non-limiting examples of common catheter materials are polyethylene and silicone. Preferably, the catheter material is loaded with between about 20 and 80 weight percent of a radiopaque material, such as tungsten, bismuth, and the like. The addition of radiopaque agents to catheters is a well established technique, and the skilled artisan can readily determine an appropriate radiopaque agent, and an optimum loading for a particular catheter.

The inventive central venous catheter may be introduced into a body vessel for use in a medical interventional procedure in well-known manner. Suitable percutaneous techniques for insertion of central venous catheters into body vessels are known in the medical arts, and are in widespread use. Perhaps the most widely-utilized technique, and the technique favored herein, is the well-known Seldinger technique. In the Seldinger technique, an injection is made into the vessel interior with a needle, and a wire guide is inserted into the vessel through a bore in the needle. The needle is withdrawn, and an introducer sheath, such as a splittable sheath like the PEEL-AWAY® sheath, available from Cook Incorporated, of Bloomington, Ind., is introduced over the wire guide. The central venous catheter is then introduced into the vessel via the introducer sheath and over the wire guide. The wire guide and the sheath are removed in conventional fashion, leaving the central venous catheter in the body vessel.

Other details related to the composition, formation and use of central venous catheters are well known in the art, and are not considered crucial to an understanding of the present invention. Accordingly, such details have not been included herein.

If desired, the inventive central venous catheter may be supplied as a system or kit that includes, among other things, an introducer needle, one or more dilators, a straight or curved wire guide, injection caps, and a syringe. The accessories, as well as the central venous catheters, can be made available in a variety of sizes and compositions for use with a particular patient. These accessories are well known in the art, and are commonly provided by manufacturers, such as Cook Incorporated, of Bloomington, Ind., in conjunction with central venous catheters.

While this invention has been particularly shown and described with reference to preferred embodiments thereof, it will be understood by those skilled in the art that various changes in form and details may be made therein without departing from the spirit and scope of the invention. Those skilled in the art may recognize or be able to ascertain using no more than routine experimentation, many equivalents to the specific embodiments of the invention described specifically herein, which equivalents are intended to be encompassed in the scope of the invention.

The invention claimed is:

1. A central venous catheter comprising: a catheter body having a proximal end and a distal end, and having a plurality of lumens extending longitudinally therein; a first one of said lumens extending longitudinally through the catheter body from said proximal end to an exit port at said distal end; and a second one of said lumens extending longitudinally through the catheter body to a closed distal portion of said catheter body, said catheter body further including a sideport positioned along a length of said catheter body to establish communication between said second lumen and an area exterior to said catheter body; said second lumen comprising a dead space disposed between said sideport and said closed distal portion, and a flexible helical member having a proximal end and a distal end, said flexible helical member disposed within said dead space such that said proximal end is distal to said sideport.

2. The catheter of claim 1, wherein said flexible helical member comprises a coil.

3. The catheter of claim 2, wherein said coil comprises stainless steel.

4. The catheter of claim 2, wherein said coil comprises a metallic alloy.

5. The catheter of claim 4, wherein said metallic alloy comprises nitinol.

6. The catheter of claim 2, wherein said flexible helical member comprises a cannula having a generally helical shape cut into a body of the cannula.

7. The catheter of claim 6, wherein said cannula comprises a superelastic material.

8. The catheter of claim 7, wherein said superelastic material comprises nitinol.

9. The catheter of claim 1, wherein the flexible helical member is bonded to a wall of said second lumen along at least a portion of a length of said flexible helical member.

10. The catheter of claim 1, wherein said central venous catheter comprises respective entry ports proximal of said catheter body in communication with respective lumens.

11. The catheter of claim 10, wherein said central venous catheter further comprises respective extension tubes for providing said communication between said entry ports and said lumens.

12. The catheter of claim 1, wherein said plurality of lumens comprises two lumens.

13. The catheter of claim 1, wherein said plurality of lumens further comprises a third lumen, said third lumen extending longitudinally through the catheter body to a closed distal portion of said catheter body; and wherein said catheter body includes a second sideport to establish communication between said third lumen and an area exterior of said catheter body, said third lumen comprising a dead space disposed between said second sideport and said closed distal portion.

14. The catheter of claim 13, wherein said first and second sideports are longitudinally spaced along the length of said catheter body.

15. The catheter of claim 14, wherein said first and second sideports are oriented in a spiral-like configuration along the length of said catheter body.

16. The catheter of claim 13, wherein each of said lumens is in communication at said catheter body proximal end with a respective entry port.

17. The catheter of claim 13, wherein said third lumen dead space includes a flexible member disposed therein.

18. The catheter of claim 17, wherein said flexible member in said third lumen comprises a helical coil.

19. The catheter of claim 17, wherein at least one of said flexible members comprises a metallic alloy.

20. The catheter of claim 17, wherein at least one of said flexible members comprises a cannula, said cannula having a generally helical shape cut into a body of the cannula.

21. The catheter of claim 17, wherein at least one of said flexible members occupies substantially the entire length of said dead space.

22. The catheter of claim , wherein at least a portion of said catheter body is coated with an antimicrobial component.

23. The catheter of claim 22, wherein said antimicrobial component comprises at least one of minocycline and rifampin.

* * * * *

UNITED STATES PATENT AND TRADEMARK OFFICE
CERTIFICATE OF CORRECTION

PATENT NO. : 7,311,697 B2
APPLICATION NO. : 10/878752
DATED : December 25, 2007
INVENTOR(S) : Thomas A. Osborne Page 1 of 1

It is certified that error appears in the above-identified patent and that said Letters Patent is hereby corrected as shown below:

<u>Column 8</u>
Line 60, add -- 1 -- after "claim" and before ",".

Signed and Sealed this

Twenty-ninth Day of April, 2008

JON W. DUDAS
*Director of the United States Patent and Trademark Office*